US007541435B2

(12) United States Patent
Proudfoot et al.

(10) Patent No.: US 7,541,435 B2
(45) Date of Patent: Jun. 2, 2009

(54) ANTAGONISTS OF CXCR3-BINDING CXC CHEMOKINES

(75) Inventors: Amanda Proudfoot, Chens sur Leman (FR); Marie Kosco-Vilbois, Minzier (FR)

(73) Assignee: Merck Serono SA, Coinsins, Vaud (CH)

( * ) Notice: Subject to any disclaimer, the term of this patent is extended or adjusted under 35 U.S.C. 154(b) by 264 days.

(21) Appl. No.: 10/517,726

(22) PCT Filed: Jun. 3, 2003

(86) PCT No.: PCT/EP03/50211

§ 371 (c)(1), (2), (4) Date: Jan. 26, 2006

(87) PCT Pub. No.: WO03/106488

PCT Pub. Date: Dec. 24, 2003

(65) Prior Publication Data

US 2006/0204498 A1 Sep. 14, 2006

(30) Foreign Application Priority Data

Jun. 12, 2002 (EP) .................................. 02100697

(51) Int. Cl.

| | |
|---|---|
| ***C07K 14/00*** | (2006.01) |
| ***A61K 45/00*** | (2006.01) |
| ***A61K 39/00*** | (2006.01) |
| ***C07H 21/04*** | (2006.01) |
| ***C12P 21/02*** | (2006.01) |

(52) U.S. Cl. ................... 530/351; 424/85.1; 424/185.1; 424/198.1; 536/23.5; 435/69.5

(58) Field of Classification Search ....................... None
See application file for complete search history.

(56) References Cited

U.S. PATENT DOCUMENTS

| | | | |
|---|---|---|---|
| 5,656,724 | A | 8/1997 | Daly et al. |
| 5,739,103 | A | 4/1998 | Rollins et al. |
| 5,969,093 | A | 10/1999 | Jacobs et al. |
| 5,977,334 | A | 11/1999 | Ransohoff et al. |
| 6,140,064 | A | 10/2000 | Loetscher et al. |
| 2002/0018776 | A1 | 2/2002 | Hancock |

FOREIGN PATENT DOCUMENTS

| | | | |
|---|---|---|---|
| WO | WO 02/04015 | A1 | 1/2002 |
| WO | WO 02/43758 | A2 | 6/2002 |

OTHER PUBLICATIONS

Widney D.P. et al. The murine chemokine CXCL11 (IFN-inducible T cell a-chemoattractant) is an IFN-g- and lipopolysaccharide-inducible glucocorticoid-attenuated response gene expressed in lung and other tissues during endotoxemia. J. Immunol. 2000. vol. 164, p. 6322-6331.*

Mickle J.E. et al. Genotype-phenotype relationships in cystic fibrosis. Med. Clin. N. America. 2000, vol. 84, p. 597-607.*

Loertscher, P. et al. "The Ligands of CXC Chemokine Receptor 3, I-TAC, Mig, and IP10, Are Natural Antagonists for CCR3" *The Journal of Biological Chemistry*, Feb. 2, 2001, pp. 2986-2991, vol. 276, No. 5.

* cited by examiner

*Primary Examiner*—Robert Landsman
*Assistant Examiner*—Bruce D Hissong
(74) *Attorney, Agent, or Firm*—Saliwanchik, Lloyd & Saliwanchik

(57) ABSTRACT

Novel antagonists of CXCR3-binding CXC chemokines, and in particular of human CXCL11, can be obtained by generating mutants of such chemokines in which the binding to glycosaminoglycans (GAGs) is impaired due to non-conservative substitutions of amino acids involved in this interaction. Compounds prepared in accordance with the present invention can be used to block the activity of CXCR3-binding CXC chemokines on CXCR3-expressing cells, thereby providing therapeutic compositions for use in the treatment or prevention of diseases related to excessive activated T cells migration, such as graft rejection and autoimmune diseases, and of diseases needing an increase of vascularization, such as ischemic heart disease.

23 Claims, 7 Drawing Sheets

```
                    10        20        30        40        50        60        70
                     |         |         |         |         |         |         |
CXCL11-WT   FPMFKRGRCLCIGPGVKAVKVADIEKASIMYPSNNCDKIEVIITLKENKGQRCLNPKSKQARLIIKKVERKNF
CXCL11-1B3  FPMFAAGACLCIGPGVKAVKVADIEKASIMYPSNNCDKIEVIITLKENKGQRCLNPKSKQARLIIKKVERKNF
CXCL11-2B3  FPMFKRGRCLCIGPGVKAVKVADIEKASIMYPSNNCDKIEVIITLAENAGQACLNPKSKQARLIIKKVERKNF
CXCL11-3B3  FPMFKRGRCLCIGPGVKAVKVADIEKASIMYPSNNCDKIEVIITLKENKGQRCLNPASAQAALIIKKVERKNF
CXCL11-4B4  FPMFKRGRCLCIGPGVKAVKVADIEKASIMYPSNNCDKIEVIITLKENKGQRCLNPKSKQARLIIAAVEAANF
```

B)

```
                 10        20        30        40        50        60        70
                  |         |         |         |         |         |         |
mCXCL11  FLMFKQGRCLCIGPGMKAVKMAEIEKASVIYPSNGCDKVEVIVTMKAHKRQRCLDPRSKQARLIMQAIEKKNFLRRQNM
hCXCL11  FPMFKRGRCLCIGPGVKAVKVADIEKASIMYPSNNCDKIEVIITLKENKGQRCLNPKSKQARLIIKKVERKNF
hCXCL10  VPLSRTVRCTCISISNQPVNPRSLEKLEIIPASQFCPRVEIIATMKKKGEKRCLNPESKAIKNLLKAVSKEMSKRSP
hCXCL9   TPVVRKGRCSCISTNQGTIHLQSLKDLKQFAPSPSCEKIEIIATLK-NGVQTCLNPDSADVKELIKKWEKQVSQKKKQK
         ....B..BC.C.......................C.B.......B......C........B...B...B
```

ANTAGONISTS OF CXCR3-BINDING CXC CHEMOKINES

CROSS-REFERENCE TO RELATED APPLICATION

This application is the U.S. national stage application of International Patent Application No. PCT/EP03/50211, filed Jun. 3, 2003.

FIELD OF THE INVENTION

The invention relates to structure and the properties of antagonists of CXCR 3-binding CXC chemokines, and in particular of human CXCL11.

BACKGROUND OF THE INVENTION

Chemokines are secreted pro-inflammatory proteins of small dimensions (70-130 amino acids) mostly involved in the directional migration and activation of cells, especially the extravasation of leukocytes from the blood to tissue localizations needing the recruitment of these cells (Baggiolini M et al., 1997; Fernandez E J and Lolis E, 2002).

Depending on the number and the position of the conserved cysteines in the sequence, chemokines are classified into C, CC, CXC and $CX_3C$ chemokines. A series of cell membrane receptors, all heptahelical G-protein coupled receptors, are the binding partners that allow chemokines to exert their biological activity on the target cells, which present specific combinations of receptors depending from their state and/or type. The physiological effects of chemokines result from a complex and integrated system of concurrent interactions: the receptors often have overlapping ligand specificity, so that a single receptor can bind different chemokines, as well a single chemokine can bind different receptors.

Usually chemokines are produced at the site of an injury, inflammation, or other tissue alteration in a paracrine or autocrine fashion. However, cell-type specific migration and activation in inflammatory and immune processes is not the sole activity of chemokines, but other physiological activities, such as hematopoiesis or angiogenesis, appear to be regulated by certain of these proteins.

Even though there are potential drawbacks in using chemokines as therapeutic agents (tendency to aggregate and promiscuous binding, in particular), chemokines offer the possibility for therapeutic intervention in pathological conditions associated to such processes, in particular by inhibiting specific chemokines and their receptors at the scope to preventing the excessive recruitment and activation of cells, in particular leukocytes (Proudfoot A, 2000; Baggiolini M, 2001; Haskell C A et al., 2002).

Amongst chemokine receptors, CXCR3 (also known as G Protein-Coupled Receptor 9 or GPR9) is a membrane receptor which is highly expressed in IL-2 activated T cells (for example CD4+ CD8+ T lymphocytes), Natural Killer cells, B cells, and (at lower levels and/or in cell cycle-restricted manner) in other non-hemopoietic cell types, such as neurons, mammary gland cells, and proximal tubule cells.

The peculiarity of CXCR3 is that, unlike other chemokine receptors, it shows a reduced number of specific CXC chemokine ligands (CXCLs): CXCL9 (also known as Monokine Induced by Gamma Interferon, MIG, Small Inducible Cytokine Subfamily B Member 9, or SCYB9), CXCL10 (also known as Interferon-Gamma-Inducible Protein 10, IP-10, Small Inducible Cytokine Subfamily B Member 10, or SCYB10), and CXCL11 (also known as Interferon-inducible T cell Alpha Chemoattractant, I-TAC, Interferon-Gamma-Inducible Protein 9, IP-9, H174, beta-R1, Small Inducible Cytokine Subfamily B Member 11, or SCYB11).

These three chemokines not only have an affinity in the nanomolar range for CXCR3, but share other important features: many amino acids are conserved amongst their sequences, all lack the "ELR" motif at the amino-terminus, they are all induced by gamma-Interferon, and all seem to have a prominent role not only in leukocyte (Th1 cells) migration in relationship not only with inflammation and autoimmunity but also with graft rejection and ischemia. These activities have been demonstrated in animal models, such as knock-out mice and mice treated with antibodies specific for the chemokine or the receptor. For example, the administration of antibodies directed against the extracellular domains of CXCR3, or against its ligands, results in the specific inhibition of the inflammatory responses mediated by this receptor (WO 01/72334; WO 01/78708; WO 02/15932).

The prior art shows many evidences on the molecular mechanisms associated to the interaction between CXCR3 and its ligands, and on their importance for human physiology. When compared to CXCL9 and CXCl10, CXCL11 appears to be the most potent inducer of CXCR3-mediated activation, internalization and of transendothelial migration in human and mouse leukocytes (Cole K et al., 1998; Lu B, et al. 1999, Sauty A et al., 2001). The activity or the expression of these molecules can be considerably up-regulated and modulated in relationship to various pathological conditions, as shown in animal models or clinical samples associated to graft rejection (Meyer M et al., 2001), tubercolosis (Sauty A et al., 1999), transplant coronary artery disease (Kao J et al., 2003), HIV-1 replication (Lane B R et al., 2003), type 1 diabetes (Frigerio S et al., 2002), ulceration of intestinal epithelium (Sasaki S et al., 2002), microbial infection (Cole A et al., 2001), sarcoid granulomatous reactions (Agostini C et al., 1998), atherosclerotic lesions (Mach F et al., 1999), multiple sclerosis (Sorensen T et al., 1999; WO02/098346), cancer (Trentin L et al., 1999; Robledo M M et al., 2001), skin diseases (WO 02/43758; Flier J et al., 2001), nephropathies (Romagnani P et al., 1999), thyroid diseases (Romagnani P et al., 2002), brain or spinal cord injuries (WO 03/006045), and many other autoimmune or inflammatory diseases.

Moreover, it has also been observed that the proliferation of endothelial cells can be modulated by the interaction between CXCR3 and its ligands (Luster A et al., 1995; Romagnani P et al., 2001). CXCR3-binding CXC chemokines show an angiostatic activity on endothelial cells, which can be inhibited by anti-CXCR3 antibodies, suggesting a strict relationship between the activation of this receptor and the cell cycle regulation, at least in endothelium.

Studies on structure-activity relationships indicate that chemokines have two main sites of interaction with their receptors, the flexible amino-terminal region and the conformationally rigid loop that follows the second cysteine. Chemokines are thought to dock onto receptors by means of the loop region, and this contact is believed to facilitate the binding of the amino-terminal region that results in receptor activation. This importance of the amino-terminal region has been also demonstrated by testing natural and synthetic chemokines in which this domain is modified or shortened. This processing, following proteolytic digestion, mutagenesis, or chemical modification of amino acids, can either activate or render these molecules completely inactive, generating compounds with agonistic and/or antagonistic activity (U.S. Pat. No. 5,739,103; WO 02/59301).

These observations suggest that regulation of leukocyte recruitment during inflammatory or immune reactions is based on a combination of such agonistic and antagonistic effects, as shown for the CXCR3-binding CXC chemokines and many other chemokines (Loetscher P and Clark-Lewis I, 2001; Lambeir A et al., 2001). Thus, chemokines with specific modifications in the amino-terminal region are considered having therapeutic potential for inflammatory and autoimmune diseases (Schwarz and Wells, 1999).

As many other cell-signaling soluble molecules (interleukins, growth factors), chemokines show physiological interactions not only with cell receptors but also with glycosaminoglycans (GAGs), although with varying affinities. These negatively charged molecules are formed by disaccharide repeats (such as heparin, chondroitin sulfate, heparan sulfate, dermatan sulfate, and hyaluronic acid) and naturally occur on cell surfaces, in the extracellular matrix, or in the circulation. They can be present in isolated forms or linked to proteins (proteoglycans, or PGs) following the post-translational addition of GAGs at serine residues.

Chemokines, as the other GAG-binding proteins, have basic residues (mainly Arginine and Lysine) clustered in short portions of their sequence which are suitable for this purpose but such motifs are structured in different manner for each chemokine, or group of highly homologous chemokines. Some of these GAG-binding sites have been associated to specific consensus, such as BBXB motifs (where B represents a basic residue, and X any other residue) or other arrangements (Kuschert G et al., 1999; Proudfoot A et al., 2001).

The main consequence of this interaction is the aggregation of the chemokines, a state which is believed to provide a protection from proteolysis, as well as a mechanism for the controlled and gradient-generating release of the chemokines, participating to the recognition and to the presentation of chemokines to the receptors as oligomers (Hoogewerf A J et al., 1997; Kuschert G et al., 1999). The interaction with GAGs and the formation of these gradients has been clearly demonstrated for many chemokines, and the relative affinity has been measured. Therefore, it has been suggested that also the modulation of such interactions may represent a therapeutic approach in inflammatory disease (Ali S et al., 2001; Patel D et al., 2001).

Means to achieve a therapeutic effect on the basis of the GAGs-chemokines interactions known in the art involve the generation of GAGs analogs modulating the interaction between endogenous GAGs and chemokines (WO 94/20512), the use of heparanase for eliminating GAGs (WO 97/11684), the administration of chemokine-GAGs complexes (WO 99/62535), the modification of GAGs binding domain with polymers (WO 02/04015), or the substitution of residues involved in GAG-binding activity (WO 02/28419).

Even though extensive studies have been performed on some chemokines, it is well established that is not possible to anticipate, on the basis of the sequence homology with chemokine having limited similarity or known GAG-binding protein motifs, which specific basic residues have to be modified with non-conservative substitutions to impair GAG-binding, since there is a significant structural diversity of GAG-binding domains amongst the chemokine protein family (Lortat-Jacob H et al., 2002). Methods of detecting or identifying ligands, inhibitors or promoters of CXCR3 are also known in the art (U.S. Pat. No. 6,140,064). However, none of these approaches can be actually applied for generating and studying GAG-binding defective CXCL9, CXCL10, or CXCL11. Structural requirements for the interaction with GAGs, neither their tridimensional structure, are known for CXCR3 and for its ligands. There is no disclosure in the prior art of which may be the residues of these chemokines involved in GAG-binding, as well the in vivo effects deriving from their non-conservative substitution in mutant proteins.

SUMMARY OF THE INVENTION

It has been found that specific basic residues in the carboxyl-terminus of a human CXCR3-binding CXC chemokine (CXCL11) are responsible for the interaction with glycosaminoglycans (GAGs).

The elimination of these basic residues by non-conservative substitutions (for example, with Alanines) leads to the generation of CXCL11 mutants having not only have a considerably reduced tendency to interact with GAGs, but an in vivo antagonistic activities on CXCL11. Such evidences can be exploited to use mutants of CXCL11 and of the most similar CXCR3-binding CXC chemokines (CXCL10 and CXCL9), as antagonists of the corresponding natural chemokines. Compounds prepared in accordance with the present invention can be used to block the activity of CXCR3-binding CXC chemokines on CXCR3-expressing cells, thereby providing therapeutic compositions for use in the treatment of diseases related to excessive activated T cells migration, such as graft rejection and autoimmune diseases (rheumatoid arthritis, multiple sclerosis, type 1 diabetes), of cancer, of HIV-1 infection, and of diseases needing an increase of vascularization, such as ischemic heart disease.

Other features and advantages of the invention will be apparent from the following detailed description.

DESCRIPTION OF THE FIGURES

FIG. 1: (A) amino acid sequences of mature human CXCL11 (CXCL11-WT; SEQ ID NO: 1) and of the mutants generated on the basis of this sequence, which have been expressed and tested as described in the Examples (mutated amino acids are bold and underlined; SEQ ID NO: 2-5). The numbering is based on the mature human sequence, which lacks a 21 amino acids-long signal peptide. (B) Alignment of the sequence common to the mature forms of the following CXCR3 binding CXC chemokines: mouse CXCL11 (mCXCL11; SWISSPROT Acc. N° Q9JHH5; SEQ ID NO: 8), human CXCL11 (hCXCL11; SWISSPROT Acc. N° O14625; SEQ ID NO: 1), human CXCL10 (hCXCL10; SWISSPROT Acc. N° P02778; SEQ ID NO: 6), and human CXCL9 (hCXCL9; SWISSPROT Acc. N° Q07325; SEQ ID NO: 7). Bold and underlined residues in human CXCL11 sequence have been mutagenized to Alanine in the different variants presented in the Examples (residues 5, 6, 8, 46, 49, 52, 57, 59, 62, 66, 67, 70 and 71). The other basic residues of human CXCL11, and all the basic residues in mouse CXCL11, human CXCL10, and human CXCL9 are underlined. Cysteines and basic residues conserved amongst human CXCR3-binding CXC chemokines are indicated in the boxed line below the alignment, respectively, as C and B. The numbering is based on the mature human sequences, which lack a signal peptide including the N-terminal 21 (mCXCL11, hCXCL11 and hCXCL10) or 22 (hCXCL9) amino acids. The mature form of mCXCL11, hCXCL11, and hCXCL10 is shown entirely, whilst the mature form of hCXCL9 has 25 more amino acids at the carboxyl-terminus.

DETAILED DESCRIPTION OF THE INVENTION

Figure 2:
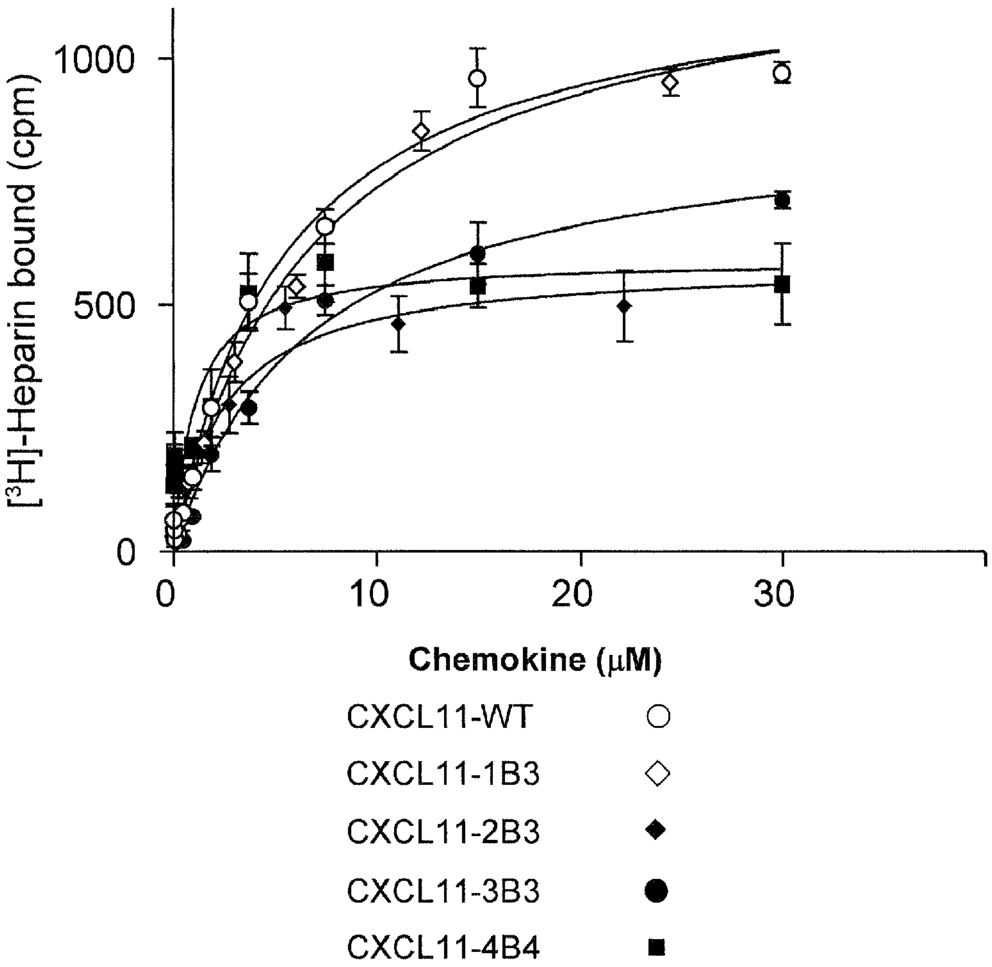
FIG. 2: graph representing the results of the heparin-binding assay performed with [$^3$H]-heparin, comparing the activity of CXCL11-WT and of the indicated CXCL11 mutants in microMolar range.

The main object of the present invention is to provide novel antagonists of CXCR3-binding CXC chemokines consisting of GAG-binding defective mutants of these chemokines in which one or more of the conserved basic residues in the carboxyl-terminus has been eliminated by non-conservative substitutions. In particular, mutants of CXCL11, CXCL10, or CXCL9 having antagonistic properties are the ones in which at least one of the following basic chosen amongst 46, 62, 66, and 70, as numbered on the sequence of human mature CXCL11, is substituted to Alanine, Glycine, Serine, Threonine, Proline, Glutammic Acid, Glutamine, Aspartic Acid, or Asparagine.

Basic residues that can be additionally mutated in preferred mutants are those conserved in one or more specific CXCR3-binding CXC chemokines (in human chemokines or across species), and/or of those surrounding those conserved basic residues. Multiple mutants are preferably generated by substituting at least two consecutive conserved basic residues in a non-conservative manner, but other possible combinations are disclosed by the present invention.

The present patent application provides in vivo and in vitro data on the binding and antagonistic activities of novel recombinant CXCL11 mutants in which specific combinations of basic residues were non-conservatively substituted with Alanines. These evidences, combined with the knowledge on the sequence and the properties of other highly conserved CXCR3-binding CXC chemokines, suggest that specific conserved basic site not only can play a general role in the biological activity of these chemokines, but can be modified, according to the present invention, to obtain a series of molecules having antagonistic properties against the natural chemokine.

In a main embodiment, antagonists of human CXCL11 consist of mutants of human CXCL11 wherein at least one of the following basic residues, numbered on the sequence of human mature CXCL11, is additionally substituted to Alanine, Glycine, Serine, Threonine, Proline, Glutammic Acid, Glutamine, Aspartic Acid, or Asparagine,: 49, 52, 57, 59, 67, or 71. More preferably, the CXCL11 mutants have one of the following combinations of basic residues, numbered on the sequence of human mature CXCL11, substituted to Alanine, Glycine, Serine, Threonine, Proline, Glutammic Acid, Glutamine, Aspartic Acid, or Asparagine:

a) 46, together with 49 and/or 52;

b) 62, together with 57 and/or 59;

c) 66 and 70, together with 67 and/ or 71; or d) 62 and 66, together with one or more of the following: 57, 59, 67, 70, or 71.

The Examples disclose mutants included in the definition of (a), (b), or (c) combination, whilst (d) combination includes two consecutive conserved basic residues, together with surrounding basic residues.

Finally, basic residues of CXCL11 that can be further mutated are those conserved in another CXCR3-binding CXC chemokine and/or across species (such as mouse). Therefore, other preferred CXCL11 mutants at least one of the following basic residues, numbered on the sequence of human mature CXCL11, is additionally substituted to Alanine, Glycine, Serine, Threonine, Proline, Glutammic Acid, Glutamine, Aspartic Acid, or Asparagine: 5, 6, 8, 17, 20, 26, or 38.

In another main embodiment, antagonists of human CXCL10 consist of mutants of human CXCL10 wherein at least one of the following basic residues, numbered on the sequence of human mature CXCL11, is additionally substituted to Alanine, Glycine, Serine, Threonine, Proline, Glutammic Acid, Glutamine, Aspartic Acid, or Asparagine: 47, 48, 51, 52, 59, 74, or 75. More preferably, the CXCL10 mutants have one of the following combinations of basic residues, numbered on the sequence of human mature CXCL11, substituted to Alanine, Glycine, Serine, Threonine, Proline, Glutammic Acid, Glutamine, Aspartic Acid, or Asparagine:

a) 46 and 52, together with 47, 48, or 51;

b) 59 and 62;

c) 66 and 70, together with 74 and/or 75; or d) 62 and 66, together with 59 and/or 70.

Finally, basic residues of CXCL10 that can be further mutated are those conserved in another CXCR3-binding CXC chemokine and/or across species (such as mouse). Therefore, other preferred CXCL10 mutants at least one of the following basic residues, numbered on the sequence of human mature CXCL11, is additionally substituted to Alanine, Glycine, Serine, Threonine, Proline, Glutammic Acid, Glutamine, Aspartic Acid, or Asparagine: 5, 8, 22, 26, or 38.

In a further main embodiment, antagonists of human CXCL9 consist of mutants of human CXCL9 wherein basic residue 67, numbered on the sequence of human mature CXCL11, is additionally substituted to Alanine, Glycine, Serine, Threonine, Proline, Glutammic Acid, Glutamine, Aspartic Acid, or Asparagine. More preferably, the CXCL9 mutants have one of the following combinations of basic residues, numbered on the sequence of human mature CXCL11, substituted to Alanine, Glycine, Serine, Threonine, Proline, Glutammic Acid, Glutamine, Aspartic Acid, or Asparagine:

a) 62, together with 66 and/or 67;

b) 66 and 67; or c) 66 and 70, together with one or more of the following: 67, 74, or 75.

Finally, basic residues of CXCL9 that can be further mutated are those conserved in another CXCR3-binding CXC chemokine and/or across species (such as mouse). Therefore, other preferred CXCL9 mutants at least one of the following basic residues, numbered on the sequence of human mature CXCL11, is additionally substituted to Alanine, Glycine, Serine, Threonine, Proline, Glutammic Acid, Glutamine, Aspartic Acid, or Asparagine: 5, 6, 8, 25, 28, or 38.

The amino acid replacing the basic residue is preferably a non-polar, small amino acid like Alanine or Glycine, but other amino acids are appropriate, provided that they have a charge and dimension which are incompatible with GAG-binding and, at the same time, poorly interfere with other properties of the protein. Amino acids suitable for the substitutions are Serine, Threonine, Proline, Glutammic Acid, Glutamine, Aspartic acid, or Asparagine. Antagonists of human CXCL11 having Alanine substitutions in combination of basic residues as defined in the present invention (FIG. 1A) have the sequence disclosed as CXCL11-2B3 (SEQ ID NO: 3), CXCL11-3B3 (SEQ ID NO: 4), or CXCL11-4B4 (SEQ ID NO: 5). The examples show how these CXCL11 mutants are heparin-binding defective and act as antagonists of the corresponding natural chemokine, being CXCL11-3B3 particularly effective.

The wording "GAG-binding defective mutants" or "heparin-binding defective mutants" means that the mutants having a lower ability to bind to GAGs in the assays disclosed in present invention (i.e. a lower percentage of each of these mutants, with respect to the corresponding wild-type molecule, bind to GAGs like heparin).

In the sense of the present application, "CXCR3-binding CXC chemokines" are the human non-ELR chemokines shown in FIG. 1B: human CXCL11 (also known as H174, Interferon inducible T-cell Alpha Chemoattractant, I-TAC, or Interferon gamma induced protein 9), human CXCL10 (also known as IP-10 or Interferon gamma induced protein 10), human CXCL9 (also known as MIG or Interferon gamma induced monokine). This definition includes as well mammalian orthologs of these sequences (such as mouse CXCL11, shown in FIG. 1B).

In view of the prior art, there is no indication that above indicated combinations of basic amino acid in the carboxyl-terminus of CXCL11 define a GAGs/heparin binding site, and that the non-conservative substitution of these residues to molecules having antagonistic activity on the corresponding natural molecule. Moreover, given the conservativity of some of basic residues included in these combinations amongst known human CXCR3-binding chemokines (CXCL10 and CXCL9), it can be inferred that the antagonists of these group of chemokines can be obtained by the non-conservative substitution of residues corresponding to the ones functionally characterized for human CXCL11 in the present patent application. Therefore, the present invention provide mutants of CXCR3-binding proteins which contain a combination of the mutations defined above, and which act as antagonists for the corresponding naturally-occurring chemokines. Compounds prepared in accordance with the present invention can be used to block the activity of CXCR3-binding CXC chemokines on CXCR3-expressing cells, thereby providing therapeutic compositions for use in the treatment of diseases related to excessive or uncontrolled production of CXCR3-binding CXC chemokines, such as autoimmune disorders or graft rejection, or for counteracting their angiostatic effects.

Further objects of the present invention are alternative molecules based on the structure and the activity of the antagonists of CXCR3-binding CXC chemokines of the present invention.

A first class of alternative molecules is represented by active mutants of the CXCR3-binding CXC chemokines antagonists defined above. These proteins should maintain, or even potentiate, the antagonistic properties of the mutants exemplified in the present patent application.

This category of molecules includes natural or artificial analogs of said sequence, wherein one or more amino acid residues have been added, deleted, or substituted, provided they display the same biological activity characterized in the present invention at comparable or higher levels, as determined by means known in the art and disclosed in the Examples below. For example, specific mutants may have one or more amino acids being added, deleted, or substituted in the amino-terminal region known to affect receptor binding. In particular, these mutations may involve one or more of the first nine amino acids of the mature human CXCR3-binding CXC chemokine positioned in the amino-terminal region, just before the conserved CXC motif (FIG. 1B). Such molecules, eventually, may contain one or more amino acids have been mutated obtaining a variant having a decreased tendency to aggregation, as shown for other chemokines (WO 98/13495).

In accordance with the present invention, preferred changes in these active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov SI and Nekrasov AN, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The synonymous amino acid groups and more preferred synonymous groups are tho se defined in Table I.

Active mutants produced by substitutions made on the basis of these teachings, as well as active mutants wherein one or more amino acids were eliminated or added, are amongst the objects of the present invention, that is, novel mutants of CXCR3 binding CXC chemokines having poor GAG binding properties and antagonistic activity on the corresponding CXCR3 binding chemokines, comparable to the ones of the initially selected mutants, or even improved if possible. Similar compounds may result from conventional mutagenesis technique of the encoding DNA, from combinatorial technologies at the level of encoding DNA sequence (such as DNA shuffling, phage display/selection), or from computer-aided design studies, followed by the validation for the desired activities as described in the prior art and in the Examples below.

A second class of alternative molecules of the invention is represented by antagonists of CXCR3-binding CXC chemokines comprising one of the amino acid sequences as defined above and an amino acid sequence belonging to a protein sequence other than the corresponding CXCR3-binding CXC chemokine. This heterologous latter sequence should provide additional properties without impairing significatively the antagonistic activity, or im proving GAG-binding properties. Examples of such additional properties are an easier purification procedure, a longer lasting half-life in body fluids, an additional binding moiety, the maturation by means of an endoproteolytic digestion, or extracellular localization. This latter feature is of particular importance for defining a specific group of fusion or chimeric proteins included in the above definition since it allows the molecules defined as CXCR3-binding CXC chemokines antagonists in this patent application to be localized in the space where not only where the isolation and purification of these polypeptides is facilitated, but also where CXCR3-binding CXC chemokines and their receptor naturally interact.

Design of the moieties, ligands, and linkers, as well methods and strategies for the construction, purification, detection and use of fusion proteins are widely discussed in the literature (Nilsson J et al., 1997; "Applications of chimeric genes and hybrid proteinsu Methods Enzymol. Vol. 326-328, Academic Press, 2000; WO 01/77137). Additional protein sequences which can be used to generate the antagonists of the present invention are chosen amongst extracellular domains of membrane-bound protein, immunoglobulin constant region, multimerization domains, extracellular proteins, signal peptide-containing proteins, export signal-containing proteins. The choice of one or more of these sequences to be fused to the GAG-binding defective mutant of CXCR3-binding CXC chemokine is functional to specific use and/or purification protocol of said agent.

A third class of alternative molecules of the invention is represented by peptide mimetics (also called peptidomimetics) of the disclosed mutants of CXCR3 binding chemokines, in which the nature of peptide or polypeptide has been chemically modified at the level of amino acid side chains, of amino acid chirality, and/or of the peptide backbone. These alterations are intended to provide antagonists with improved preparation, potency and/or pharmacokinetic properties.

For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Many other modifications providing increased potency, prolonged activity, easiness of purification, and/or increased half-life are known in the art (WO 02/10195; Villain M et al., 2001).

Preferred alternative, "synonymous" groups for amino acids derivatives included in peptide mimetics are those defined in Table II. A non-exhaustive list of amino acid derivatives also include aminoisobutyric acid (Aib), hydroxyproline (Hyp), 1,2,3,4-tetrahydro-isoquinoline-3-COOH, indoline-2carboxylic acid, 4-difluoro-proline, L-thiazolidine-4-carboxylic acid, L-homoproline, 3,4-dehydro-proline, 3,4-dihydroxy-phenylalanine, cyclohexyl-glycine, and phenylglycine.

By "amino acid derivative" is intended an amino acid or amino acid-like chemical entity other than one of the 20 genetically encoded naturally occurring amino acids. In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA).

Various methodology for incorporating unnatural amino acids derivatives into proteins, using both in vitro and in vivo translation systems, to probe and/or improve protein structure and function are disclosed in the literature (Dougherty D A, 2000). Techniques for the synthesis and the development of peptide mimetics, as well as non-peptide mimetics, are also well known in the art (Sawyer T K, 1997; Hruby V J and Balse PM, 2000; Golebiowski A et al., 2001).

The polypeptides and the peptides of the present invention can be in other alternative forms which can be preferred according to the desired method of use and/or production, for example as active fractions, precursors, salts, or derivatives.

The term "active" means that such alternative compounds should maintain the functional features of the CXCR3-binding CXC chemokines mutants of the present invention, and should be as well pharmaceutically acceptable and useful.

The term "fraction" refers to any fragment of the polypeptidic chain of the compound itself, alone or in combination with related molecules or residues bound to it, for example residues of sugars or phosphates. Such molecules can result also from other modifications which do not normally alter primary sequence, for example in vivo or in vitro chemical derivativization of peptides (acetylation or carboxylation), those made by modifying the pattern of phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the amino-/ or carboxy-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Useful conjugates or complexes of the antagonists of the present invention can be generated, using molecules and methods known in the art of the interaction with receptor or other proteins (radioactive or fluorescent labels, biotin), therapeutic efficacy (cytotoxic agents), or improving the agents in terms of drug delivery efficacy, such as polyethylene glycol and other natural or synthetic polymers (Pillai O and Panchagnula R, 2001). In the latter case, the antagonists may be produced following a site-directed modification of an appropriate residue, in the natural or mutated sequence at an internal or terminal position.

The literature provides examples of technologies for generating polymer-modified or conjugated chemokines (WO 02/04015; WO 02/20033; WO 02/02132). Any residue can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment. Also, the side chains of the genetically encoded amino acids can be chemically modified for polymer attachment, or unnatural amino acids with appropriate side chain functional groups can be employed. Polymer attachment may be not only to the side chain of the amino acid naturally occurring in a specific position of the antagonist or to the side chain of a natural or unnatural amino acid that replaces the amino acid naturally occurring in a specific position of the antagonist, but also to a carbohydrate or other moiety that is attached to the side chain of the amino acid at the target position.

Polymers suitable for these purposes are biocompatible, namely, they are non-toxic to biological systems, and many such polymers are known. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, polyorthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly (N-vinyl pyrrolidone), polyalkylenes, polyacrylamide, and copolymers thereof. Preferred polymers comprise as a sequential repeat unit ethylene oxide, such as polyethylene glycol (PEG).

The preferred method of attachment employs a combination of peptide synthesis and chemical ligation. Advantageously, the attachment of a water-soluble polymer will be through a biodegradable linker, especially at the amino-terminal region of a protein. Such modification acts to provide the protein in a precursor (or "pro-drug") form, that, upon degradation of the linker releases the protein without polymer modification.

The antagonists of the invention may be prepared by any known procedure in the art, including recombinant DNA-related technologies, and chemical synthesis technologies.

Another object of the invention are the DNA molecules comprising the DNA sequences coding for the antagonists of CXCR3-binding CXC chemokines described above, including nucleotide sequences substantially the same. "Nucleotide sequences substantially the same" includes all other nucleic acid sequences that, by virtue of the degeneracy of the genetic code, also code for the given amino acid sequences. Still another object of the invention are expression vectors which comprise the above DNAs, host cells transformed with such vectors, and the process of preparation of the antagonists described above, comprising culturing these transformed cells and collecting the expressed proteins. When the vector expresses the antagonists as a fusion protein with extracellular, export signal, or signal-peptide containing proteins, the CXCR3-binding CXC chemokine antagonists can be secreted in the extracellular space, and can be more easily collected and purified from cultured cells in view of further processing or, alternatively, the cells can be directly used or administered.

These objects of the invention can be achieved by combining the disclosure provided by the present patent application on antagonists of CXCR3-binding CXC chemokines, with the knowledge of common molecular biology techniques. Many books and reviews provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

The DNA sequence coding for the proteins of the invention can be inserted and ligated into a suitable episomal or non-/homologously integrating vectors, which can be introduced in the appropriate host cells by any suitable means to transform them (transformation, transfection, conjugation, protoplast fusion, electroporation, calcium phosphate-precipitation, direct microinjection, etc.). Factors of importance in selecting a particular plasmid or viral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species.

The vectors should allow the expression of the isolated or fusion protein including the antagonist of the invention in the Prokaryotic or Eukaryotic host cell under the control of transcriptional initiation/termination regulatory sequences, which are chosen to be constitutively active or inducible in said cell. A cell line substantially enriched in such cells can be then isolated to provide a stable cell line.

For Eukaryotic hosts (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells that have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Host cells may be either Prokaryotic or Eukaryotic. Preferred are Eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences in cloned mammalian gene products and secretes peptides bearing leader sequences (i.e., pre-peptides).

Examples of chemical synthesis technologies are solid phase synthesis and liquid phase synthesis. As a solid phase synthesis, for example, the amino acid corresponding to the carboxy-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Totally synthetic chemokines are disclosed in the literature (Brown A et al., 1996).

Purification of the synthetic or recombinant antagonists of the invention can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and which are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (High Performance Liquid Chromatography) can be used. The elution can be carried using a water-acetonitrile-based solvent commonly employed for protein purification. The invention includes purified preparations of the compounds of the invention. Purified preparations, as used herein, refers to the preparations which are at least 1%, preferably at least 5%, by dry weight of the compounds of the invention.

Another object of the present invention is the use of CXCR3-binding CXC chemokines antagonists as medicaments, in particular as the active ingredients in pharmaceutical compositions (and formulated in combination with pharmaceutically acceptable carriers, excipients, stabilizers, adjuvants, or diluents) for treating or preventing diseases related to an undesirable activity of CXCR3-binding CXC chemokines leading to an excessive migration and activation of leukocytes expressing their receptors, such as autoimmune and inflammatory diseases, as well as cancer or bacterial/viral infections. Non-limitative examples of such diseases are the following: arthritis, rheumatoid arthritis (RA), psoriatic arthritis, osteoarthritis, systemic lupus erythematosus (SLE), systemic sclerosis, scleroderma, polymyositis, glomerulonephritis, fibrosis, liver or lung fibrosis and inflammation, allergic or hypersensitvity diseases, dermatitis, asthma, chronic obstructive pulmonary disease (COPD), inflammatory bowel disease (IBD), Crohn's diseases, ulcerative colitis, multiple sclerosis, septic shock, HIV infection, graft rejection, and vascular inflammation related to atherosclerosis.

In view of the prior art disclosing the specific angiostatic activity of CXCR3-binding CXC chemokines, the antagonists of the present invention may be used as active ingredients in pharmaceutical compositions for the treatment or prevention of diseases needing an increase of vascularization, as it occurs in pathological conditions such as ischemic artery disease, stroke, and delayed wound healing. The stimulation of new blood vessel growth resulting from antagonizing angiostatic factors can help the treatment of these conditions by restoring a proper circulation.

Another object of the present invention are pharmaceutical composition containing, as active ingredient, an antagonist of CXCR3-binding CXC chemokines in the forms defined above: proteins, peptide mimetics, derivatives, precursors, as well as DNA coding or cells expressing them. The process for the preparation of such pharmaceutical compositions for the treatment or prevention of diseases related to excessive leukocyte migration and activation, or to diseases needing an increase of vascularization, comprises combining this antagonist of CXCR3-binding CXC chemokines together with a pharmaceutically acceptable carrier.

Another object of the present invention is also the method for treating or preventing any of the above mentioned diseases comprising the administration of an effective amount of an antagonist of CXCR3-binding CXC chemokines of the present invention.

The pharmaceutical compositions may contain, in addition to the antagonist of CXCR3-binding CXC chemokines, suitable pharmaceutically acceptable carriers, biologically compatible vehicles and additives which are suitable for administration to an animal (for example, physiological saline) and eventually comprising auxiliaries (like excipients, stabilizers, adjuvants, or diluents) which facilitate the processing of the active compounds into preparations which can be used pharmaceutically. Such compositions can be eventually combined with another therapeutic composition acting synergically or in a coordinated manner with the antagonist of CXCR3-binding CXC chemokines of the invention. For example, similar synergistic properties of CC-chemokine antagonists have been demonstrated in combination with cyclosporin (WO 00/16796). Alternatively, the other composition can be based with a compound known to be therapeutically active against the specific disease (for example, IFN-beta for multiple sclerosis, soluble TNF receptors for rheumatoid arthritis).

The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

An "effective amount" refers to an amount of the active ingredients that is sufficient to affect the course and the severity of the disease, leading to the reduction or remission of such pathology. The effective amount will depend on the route of administration and the condition of the patient.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desiredr results. Second or subsequent administrations can be performed at a dosage, which is the same, less than, or greater than the initial or previous dose administered to the individual.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

In Vitro Characterization of the Heparin Binding Properties of CXCL11 Mutants Materials and Methods Expression of the Human CXCL11 Mutants.

Human CXCL11 mutants were generated by in vitro PCR mutagenesis of the DNA sequence coding for human CXCL11 (I-TAC; SWISSPROT Acc. N° 014625), and in particular for the mature form, corresponding to the segment 22-94 of the precursor molecule, containing 73 amino acids (CXCL11-WT; FIG. 1; SEQ ID NO: 1).

The clusters of point mutations associated to each mutein (CXCL11-1B3, SEQ ID NO: 2; CXCL11-2B3, SEQ ID NO: 3; CXCL11-3B3, SEQ ID NO: 4; CXCL11-4B4, SEQ ID NO: 5; FIG. 1A) were introduced in the coding sequence of CXCL11-WT by using one or two PCR steps of 25 cycles (proof-reading Pwo DNA polymerase; Boehringer-Mannheim). The template was a plasmid based on the commercial vector pET-24d (Novagen), in which the sequence of mature human CXCL11 is expressed as a fusion protein having a amino-terminal tag (MKKKWP) followed by a Caspase 8 cleavage site (LETD). The resulting 0.3 Kb DNA fragments obtained by PCR were digested with BspHI and XhoI, and subcloned into an empty pET-24d plasmid between the XhoI and NcoI sites. CXCL11-WT and all the muteins, lacking a starting Methionine in the mature form, can be produced as proteins containing 73 residues without any other additional residues, since the amino-terminal tag is eliminated using Caspase 8 endoproteolytic digestion.

CXCL11-WT and the muteins were expressed and tested according to methods known in art ("Chemokine Protocols", Methods in Molecular Biology, vol. 138, Humana Press, 2000). All constructs were obtained and controlled by standard molecular biology technologies (PCR mutagenesis and amplification, DNA sequencing, restriction digestion), and then maintained in the TG1 strain of *E. coli* during the cloning process. The coding sequences were chosen in order to have an optimal codon usage for expression in *E. coli* (Kane J F et al., 1995).

The pET-24d-based plasmids encoding for CXCL-11-WT or one of its mutants were transferred in BL21 (DE3) pLysS competent *E.coli* cells, wherein protein expression was induced by addition of 1 mM isopropyl-β-D-thiogalactopyranoside (IPTG) to the culture. Cells were harvested 3.5 hours after induction and resuspended in lysis buffer (50 mM Tris/HCl pH 8, 10 mM $MgCl_2$, 5 mM Benzamidine/HCl, 1 mM DTT, 0.1 mM phenylmethylsulfonyl fluoride (PMSF), Dnase 20 mg/L). Cells were broken by three passages through the French Pressure Cell unit. The suspension was then centrifuged at 10,000×g for 60 minutes at 4° C. The inclusion body pellet containing CXCL-WT or one of the muteins was solubilised (at a concentration lower than 1 mg/ml) in 0.1 M Tris/HCl, pH 8.0, containing 6M Guanidine/HCl and 1 mM DTT, and stirred for 30 minutes at 60° C. The proteins were renatured by drop-wise dilution into a volume 10 times that of the guanidine solution of 0.1M Tris/HCl, pH 8.0 containing 0.01 mM oxidised glutathione and 0.1 mM reduced glutathione. The solution was stirred overnight at 4° C. Then the pH was adjusted to 4.5 with acetic acid, and the conductivity lowered to 20 milliSiemens by dilution with water. The solution was applied to a cation exchange column (SP Sepharose) previously equilibrated in 50 mM sodium acetate (pH 4.5) and protein was eluted with a linear gradient from 0 to 2 M NaCl in the same buffer. The fractions containing the protein of interest were pooled and dialysed against 3 changes of 1% acetic acid. Insoluble material was removed by centrifugation at 10.000×g for 30 minutes and the supernatant was lyophilized.

The amino-terminal leader sequence common to CXCL11-WT and all the muteins (MKKKWPLETD) was cleaved with caspase 8 using the following procedure. The lyophilised proteins were dissolved in 15-20 ml $H_20$ and applied to PD-10 columns previously equilibrated with Capase 8 cleavage buffer (15% glycerol, 150 mM NaCl, 25 mM Tris pH 7.5, 2 mM EDTA). After the incubation of the proteins with the proteolytic enzyme (1:100, enzyme: substrate, w/w) for 4-5 hours at room temperature, the pH of the cleavage solution was adjusted to 4.5, and the conductivity lowered to 1-2 milliSiemens by dilution with 6M urea (the reaction was repeated two or three times if needed). The cleaved proteins were separated from uncleaved protein by cation exchange chromatography on a SP Sepharose column previously equilibrated in 50 mM sodium acetate (pH 4.5) containing 6 M urea, and proteins were eluted with a NaCl gradient from 0 to 2 Molar in the same buffer. The cleaved fractions were pooled and dialysed against three changes of 1% acetic acid, lyophilise d, solubilised in 0.1% trifluoroacetic acid, and finally lyophilised again for long-term storage.

The identity of all proteins so expressed was verified by mass spectrometry, and the purity by High Pressure Liquid Chromatography (HPLC).

Construction of Cell Lines Stably Expressing Human CXCR3.

Human CXCR3 was cloned from total RNA extracted from rheumatoid arthritis synovium-isolated leukocytes by Reverse Transcription-Polymerase Chain Reaction (RT-PCR) using primers based on the human CXCR3 mRNA sequence covering the entire coding sequence (Genbank N° X95876; nucleotide from 69 to 1175). All reagents for the RT-PCR reactions are commercially available (Trizol™ and Superscript™ from Life Technologies; oligod$T_{15}$ from Promega) and were used according to the manufacturer's instructions. The resultant 1.1 kb PCR product was subcloned into the mammalian cell expression vector pCDNA3.1zeo (Invitrogen) to create pZeo-CXCR3.

Human HEK293/EBNA and L1.2 cells were transfected with purified plasmid DNA for pZeo-CXCR3 by calcium phosphate precipitation using a Calcium Phosphate Transfection Kit (Life Technologies), and positive clones were selected using Zeocin (Invitrogen) according to the manufacturer's protocol. The expression of CXCR3 was confirmed by FACS (Fluorescence-Activated Cell Sorting) analysis of individual clones using a commercial monoclonal antibody against human CXCR3 labeled with an FITC fluorophore (R&D systems; cat. no. MAB160), and by a radioligand equilibrium binding assay (see below).

Chromatographic Assays of CXCL11-WT and of its Mutants

CXCL11-WT, or each of its mutants, was loaded onto either a Heparin Sepharose column (using 50 micrograms of protein) or a SP Sepharose cation exchange column (using 50 micrograms of protein). In both cases the column was equilibrated in 50 mM Tris/HCl, pH 7.5 and 50 mM NaCl and the protein was eluted with a linear gradient of 0- 2M NaCl in the same buffer.

Heparin Binding Assay of CXCL11-WT and of its Mutants.

Serial dilutions of CXCL11-WT or of its mutants in Phosphate Buffer Saline (PBS), covering the range of 0.02-30 μM, were incubated with 2.5 μg/ml of [$^3$H]-heparin for 1 hour at 37° C. Triplicates of 20 μl of each sample were transferred to a 96 well P81 Unifilter plate (Whatman Inc) fitted with a cellulose phosphate filter. The plate was washed three times with 200 μl of PBS using a vacuum pump to remove unbound labelled heparin. The scintillation fluid (50 μl) was added to each well and radioactivity counted (1 minute/well) in a beta counter. Data were analysed using Prism® software (GraphPad).

Equilibrium Competition Receptor Binding Assays

The assays were carried out on membranes from HEK cells stably expressing CXCR3 using a Scintillation Proximity Assay (SPA), with [$^{125}$I]-CXCL11 as tracer. Radiolabelled CXCL11 (recombinant human I-TAC; Peprotech) was generated and tested according to the [$^{125}$I] supplier (Amersham; specific activity of 2200 mCi/mole), also to check for CXCR3-expressing HEK and L1.2 clones positively stained during FACS analysis.

Competitors were prepared by serial dilutions (range from $10^{-6}$ to $10^{-12}$ M) of the unlabelled CXCL11, or one of its mutant, in the binding buffer (50 mM HEPES pH 7.2, 1 mM $CaCl_2$, 5 mM $MgCl_2$, 0.15 M NaCl and 0.5% Bovine Serum Albumin). Wheat germ SPA beads (Amersham) were solubilised in PBS to 50 mg/ml, and diluted in the binding buffer to a 10 mg/ml, and the final concentration in the assay was 0.25 mg/well. Cell membranes expressing CXCR3 were stored at −80° C. and diluted in the binding buffer to 20 μg/ml. Equal volumes of membrane and beads stocks were mixed before performing the assay to reduce background. The final membrane concentration was 5 μg/well and that of [$^{125}$I]-CXCL11 was 0.05 nM. The plates were incubated at room temperature with agitation for 4 hours. Radioactivity was counted (1 minute/well) in a beta counter. Data from triplicate samples were analysed using Prism® software (GraphPad).

Results

Human CXCL11 was expressed in four mutated forms to identify the sequence and the properties of non-heparin binding variants. Target of the mutations were four clusters of basic residues, and at least one basic residue conserved in all CXCR3 binding chemokines was included in each mutein (FIG. 1).

The mature form of human CXCL11 (CXCL11-WT) and the corresponding four muteins were expressed in *E coli*, (FIG. 1A). A first mutein, CXCL11-1B3, contains three Alanine substutions eliminating a basic cluster at amino-terminal of CXCL11-WT (Lysine 5, Arginine 6, and Lysine 8). A second mutein (CXCL11-2B3) contains three Alanine substutions eliminating a basic cluster surrounding residue 50 of CXCL11-WT (Lysine 46, Lysine 49, and Arginine 52). A third mutein (CXCL11-3B3) contains three Alanine substutions eliminating a basic cluster surrounding residue 60 of CXCL11-WT (Lysine 57, Lysine 59, and Arginine 62). Finally, a fourth mutein (CXCL11-4B4) contains four Alanine substitutions eliminating a basic cluster surrounding residue 70 of CXCL11-WT (Lysine 66, Lysine 67, Arginine 70, and Lysine 71).

The effects of substitutions on the CXCL11-WT muteins properties were first tested by heparin and cation exchange chromatography. The comparison of the elution profiles on such chromatographic media provides a qualitative indication on the contribution of non-specific electrostatic interactions due to basic amino acids to the heparin binding properties (Proudfoot A et al., 2001). As shown in Table III, the difference in eluting concentration of NaCl between CXCL11-WT and each mutein is calculated on cation exchange (MonoS) column and on heparin column. The values obtained on MonoS column are then subtracted from that obtained on heparin columns. If the resulting value is positive, this indicates that the mutated residues contribute to the interaction with heparin. From this analysis, it appears that the residues mutated in CXCL11-1B3 do not contribute to the binding to heparin, whereas the ones mutated in CXCL11-2B3, CXCL11-3B3 and CXCL11-4B4 are involved in the specific recognition of GAGs.

A direct measure of binding to heparin was then performed using tritiated heparin and serial dilution of the recombinant CXCL11-WT mutants (FIG. 2). The resulting radiolabeled complexes were separated from unbound [$^3$H]-heparin by contacting the reaction with cellulose phosphate filters, which are capable to retain efficiently proteins, therefore allowing a direct evaluation of amount of the bound heparin. This assay showed that CXCL11-1B3 has heparin binding properties similar to that of CXCL11-WT, whilst all the other mutants show reduced heparin binding properties (up to 50% less bound heparin), confirming the results obtained using chromatographic assays (Table III). These evidences are of particular interest since the basic cluster mutated in CXCL11-1B3 is arranged as a motif (BBXB) much more similar to other known heparin-binding motif such the one of RANTES (Proudfoot A et al., 2001), confirming the observation on the noteworthy structural diversity and poor predictability of GAG-binding sites in chemokines (Lortat-Jacob H et al., 2002).

Figure 3:
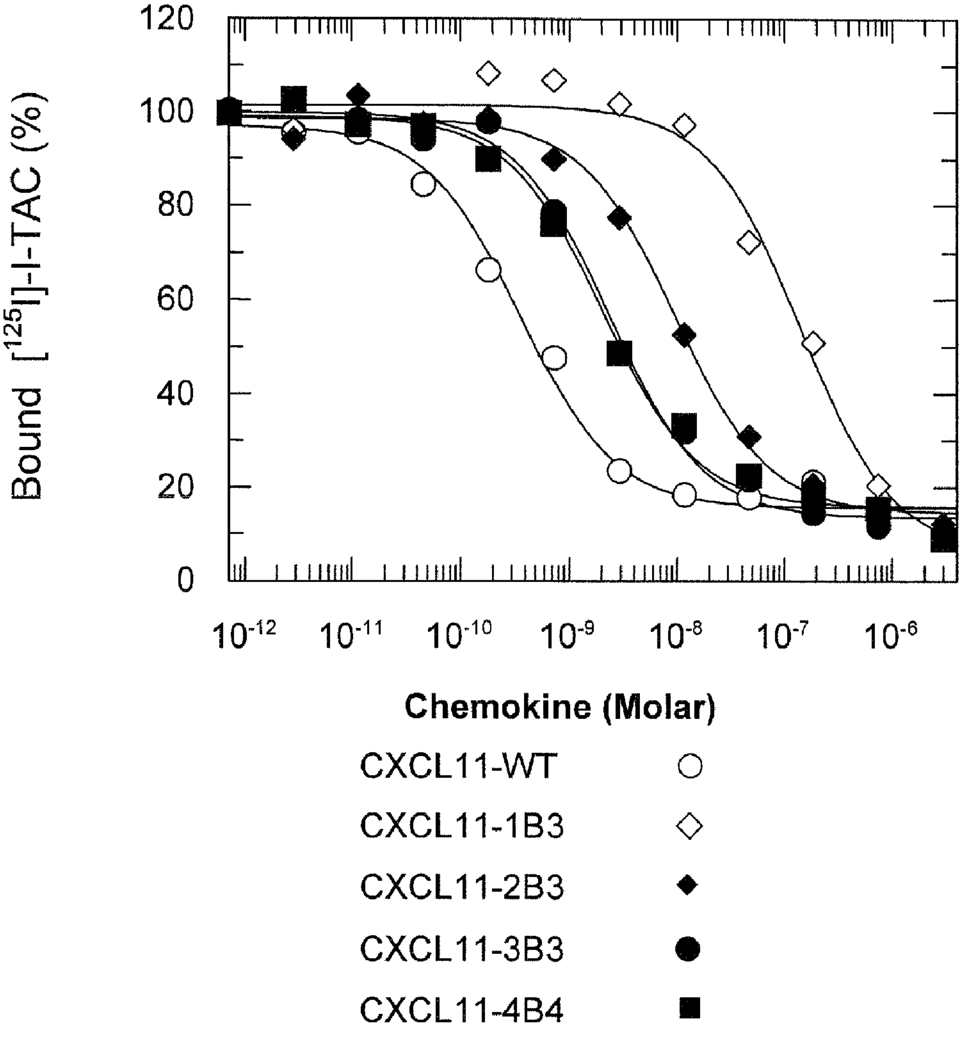
FIG. 3: graph representing the results of the equilibrium competition receptor binding assay performed by monitoring the percentage of [$^{125}$I]-CXCL11 displaced from membranes of CXCR3-expressing HEK cells, following the addition of CXCL11-WT and of the indicated CXCL11 mutants in the pico microMolar concentration range.

Finally, an equilibrium competition receptor-binding assay was performed to compare the properties of the muteins on the binding of the specific receptor CXCR3 (FIG. 3). Samples containing a constant amount of radiolabelled, commercial CXCL11 were mixed with serial dilutions of CXCL11-WT, or of one of the muteins, and then incubated with membranes prepared from CXCR3-expressing HEK cells. Whilst the heparin binding mutein CXCL11-1B3 shows a reduction of more than two orders of magnitude (changing from sub-nanomolar to sub-micromolar) in the affinity for CXCR3, the other muteins show only a limited drop in affinity for CXCR3, remaining in the nanomolar range (reduction of one order of magnitude, or less). Therefore, the affinity for the receptor is substantially retained in heparin-binding defective CXCL11-WT carboxyl-terminal mutants, whilst the mutations in amino-terminus affect specifically receptor binding, a feature which appears as clearly distinct.

Example 2

Cell-based Assay for the Characterization of a Heparin-binding Defective CXCL11 Muteins.

Materials and Methods

Chemotaxis Assay

The assay was carried out using pre-B lymphoma cell line (L1.2 cells), transfected with a plasmid allowing the expression of CXCR3 in these cells, and 96-well microplates (ChemoTX system, Neuroprobe).

CXCR3-expressing L1.2 cells (see the description above) were cultured in RPMI-1640 medium containing 5% inactivated fetal calf serum (FCS), L-glutamine, 25 mM HEPES, 0.05 mM B-Mercaptoethanol and 0.8 mg/ml Geneticin G-418. The day before the assay, 5 mM n-Butyric acid was added to the culture medium. The cells were collected by centrifugation at 600×g at room temperature and resuspended at a concentration of $1\times10^6$/ml in RPMI 1640 medium containing 5% inactivated FCS without phenol red. The receptor expression was checked by FACS analysis using an anti-CXCR3 antibody labeled with an FITC fluorophore, as described before.

The recombinant CXCL11 muteins were serially diluted (range from $10^{-6}$ to $10^{-12}$ M) in 30 μl of RPMI medium without phenol red and put in the lower wells, and a filter (8 μm pore size) was placed over them, ensuring that there are no air bubbles trapped, before sealing the system. CXCR3-expressing L1.2 cells (25 μl of a cell suspension at $2.5\times10^4$ cells/ml in the same medium) were placed in the upper wells. The chamber was incubated for 4 hours at 37° C. under 5% $CO_2$. The cell suspension was then discarded from the upper wells and the filter removed. The cells in the lower wells were transferred to a black 96 well plate and frozen for at least 1 h at −80° C. The plate was thawed and 200 μl/well of a CyQUANT dye/cell-lysis buffer mix (Molecular Probes) was added to enumerate the number of cells that had migrated. The fluorescence was counted with a Victor$^2$ Wallac plate reader. The data were analyzed using Prism® software (GraphPad).

Results

Figure 4:
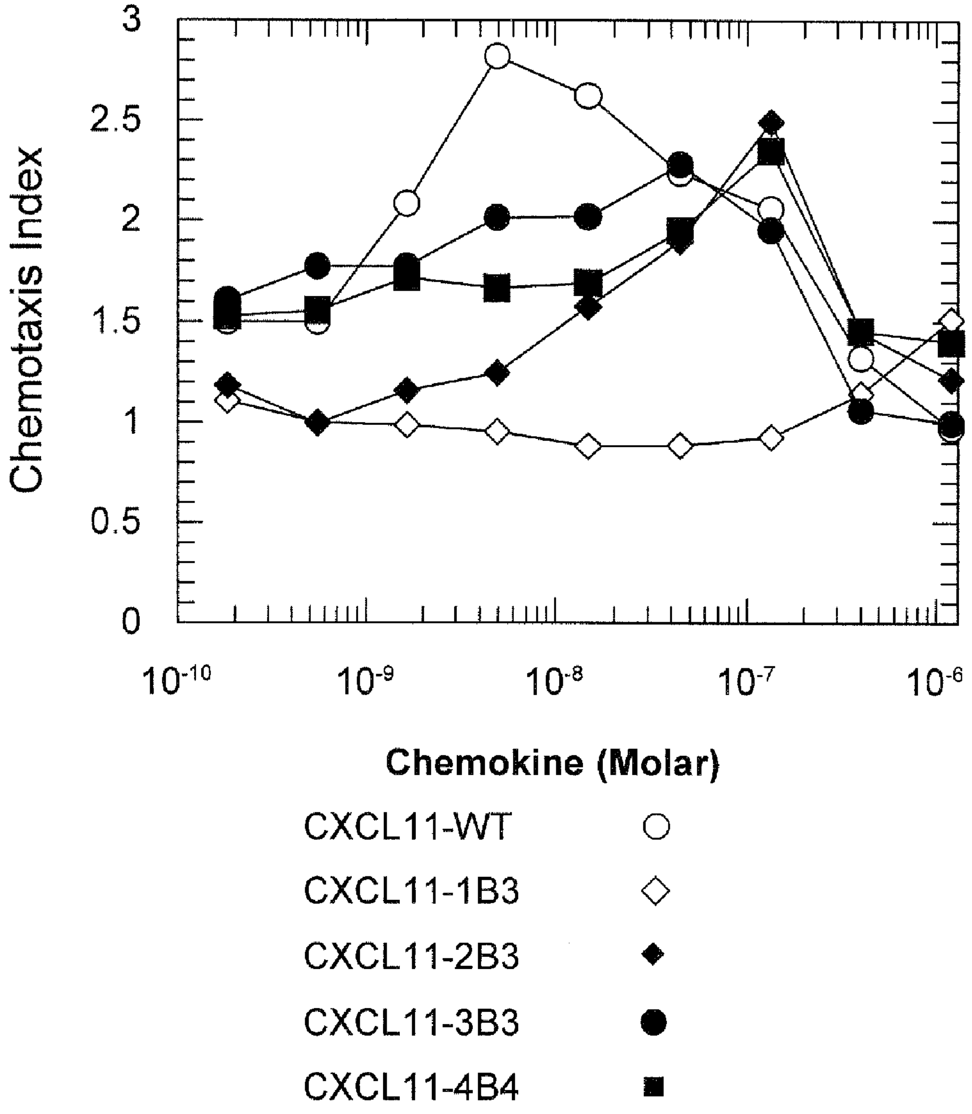
FIG. 4: graph representing the results of the chemotaxis assay performed on CXCR3-expressing L1.2 cells using CXCL11-WT or the indicated CXCL11 mutants.

The properties of CXCL11-WT muteins were tested by making use of a cell-based assay. The results obtained in a chemotaxis assay in L1.2 cells modified to express CXCR3 correspond well with those obtained in the receptor binding assay described above. In accordance with its low affinity for CXCR3, the CXCL11-1B3 mutant was unable to recruit L1.2/CXCR3 expressing cells (FIG. 4). The other three mutants were less active than CXCL11-WT, but were still able to elicit a measurable response in this chemotaxis assay.

Example 3

Animal-based Assay for the Characterization of a Heparin-binding Defective CXCL11 Muteins.

Materials and Methods

Peritoneal Cellular Recruitment

Female Balb/C mice of 8 to 12 weeks of age were sensitised on day 0. All mice received 5 sub-cutaneous injections (4×50 μl into each limb and 1×100 μl into the scruff of the neck) of 10 nM CPG-ODN (Microsynth) mixed with 100 μg Ovalbumin (Sigma, Grade V) in sterile PBS. After a week, cellular recruitment was induced into the Balb/C mice by intraperitoneal injection of 10 μg (0.5 mg/Kg) of recombinant CXCL11 protein diluted in 0.2 ml sterile, lipopolysaccharide-free saline (0.9%). When the properties of CXCL11 mutants were tested, the indicated amounts of the protein, diluted in 0.2 ml of the same sterile solution, were administered 30 minutes prior to the agonist administration. Mice were sacrificed by aerosolized $CO_2$ 4 hours later, and peritoneal lavage was performed with 5 ml PBS three times. The lavages were pooled and centrifuged at 1500×g for 5 minutes, and the pelleted cells were resuspended in a final volume of 1 milliliter. The total number of elicited leukocytes for each sample was counted with an hemacytometer.

Delayed Contact Hypersensitivity Assay

The mouse ear-swelling test to measure contact hypersensitivity was performed as described (Garrigue J L et al., 1994). Briefly, mice were pre-sensitized topically by applying 25 μl of 0.5% 2,4-dinitrofluorobenzene (DNFB; Sigma Chemical Co.) solution in acetone/olive oil (4:1) to the shaved abdomen. Five days later, 20 μl of 0.2% DNFB in the same vehicle was applied to the right ears, and vehicle alone to the left ears. Mice were treated daily from Day 5 to 9 with an intraperitoneal administration of either 0.5 mg/kg CXCL11-3B3 or vehicle only in the control group. The first treatment was administered 1 hour prior to the DNFB challenge. Ear thickness was measured with a dial thickness gauge (Mitutoyo Corp.), and ear swelling was estimated by subtracting the pre-challenge from the post-challenge value, and by further subtracting any swelling detected in the vehicle-challenged contralateral ear.

Results

Further evidences of the in vivo properties of CXCL11-WT muteins were obtained by making use of two animal models.

Figure 5:
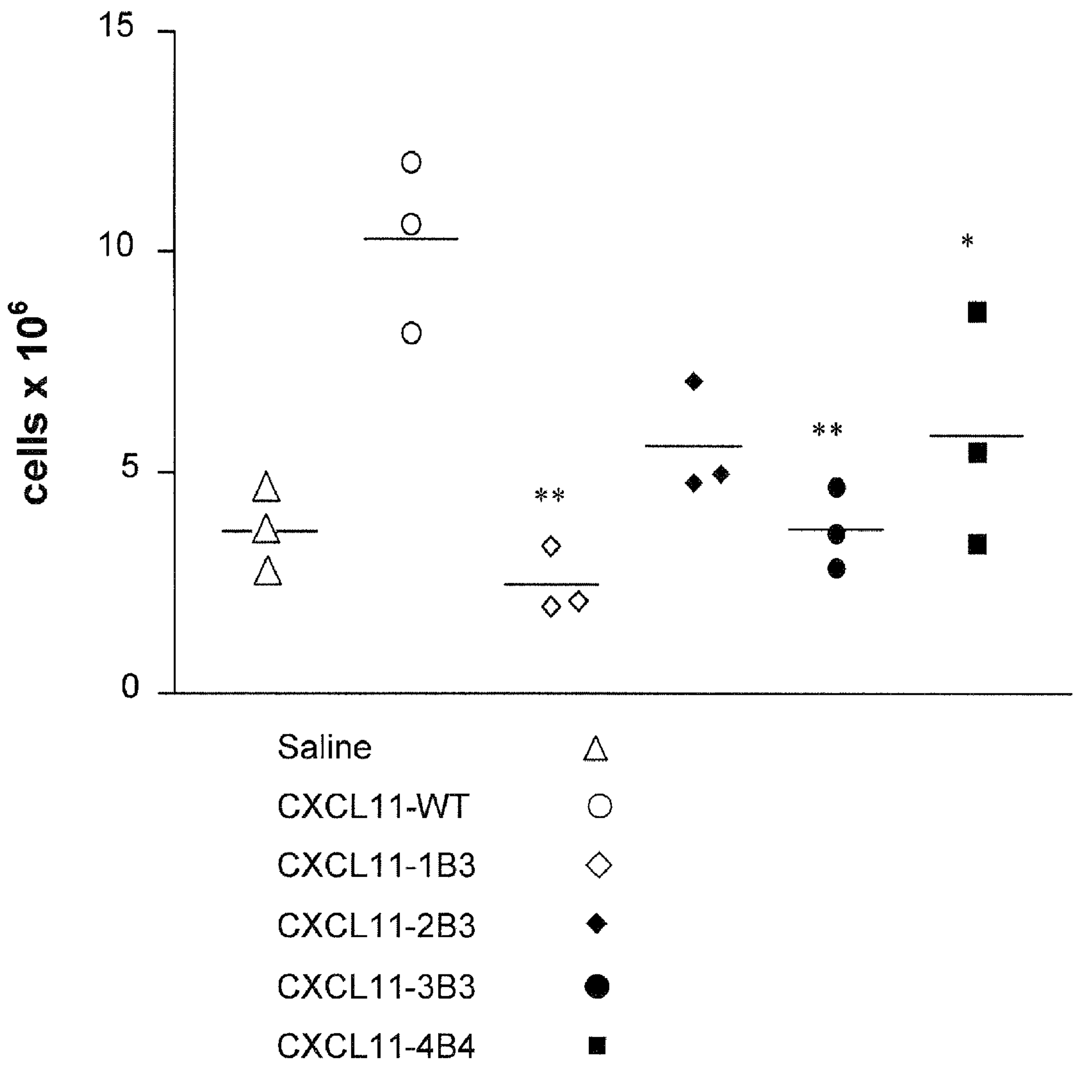
FIG. 5: graph summarizing the results of the peritoneal cell recruitment assay, performed in Female Balb/C mice using CXCL11-WT or the other indicated CXCL11 mutants, compared to a control with saline buffer. The level of statistical significance is represented with the number of asterisks.

A first assay was a peritoneal cellular recruitment assay (FIG. 5). Since CXCR3 is expressed on activated Th1 cells, mice were sensitized prior to the assay with CpG-ODN to induce a Th1 response. In accordance with its poor activity as CXCR3 binding protein and its inability to recruit cells in vitro, CXCL11-1B3 mutant was unable to recruit cells in vivo when administered into the peritoneum. Both the CXCL11-2B3 and CXCL11-4B4 showed weak activity, but the CXCL11-3B3 was not able to elicit recruitment (FIG. 5).

Figure 6:
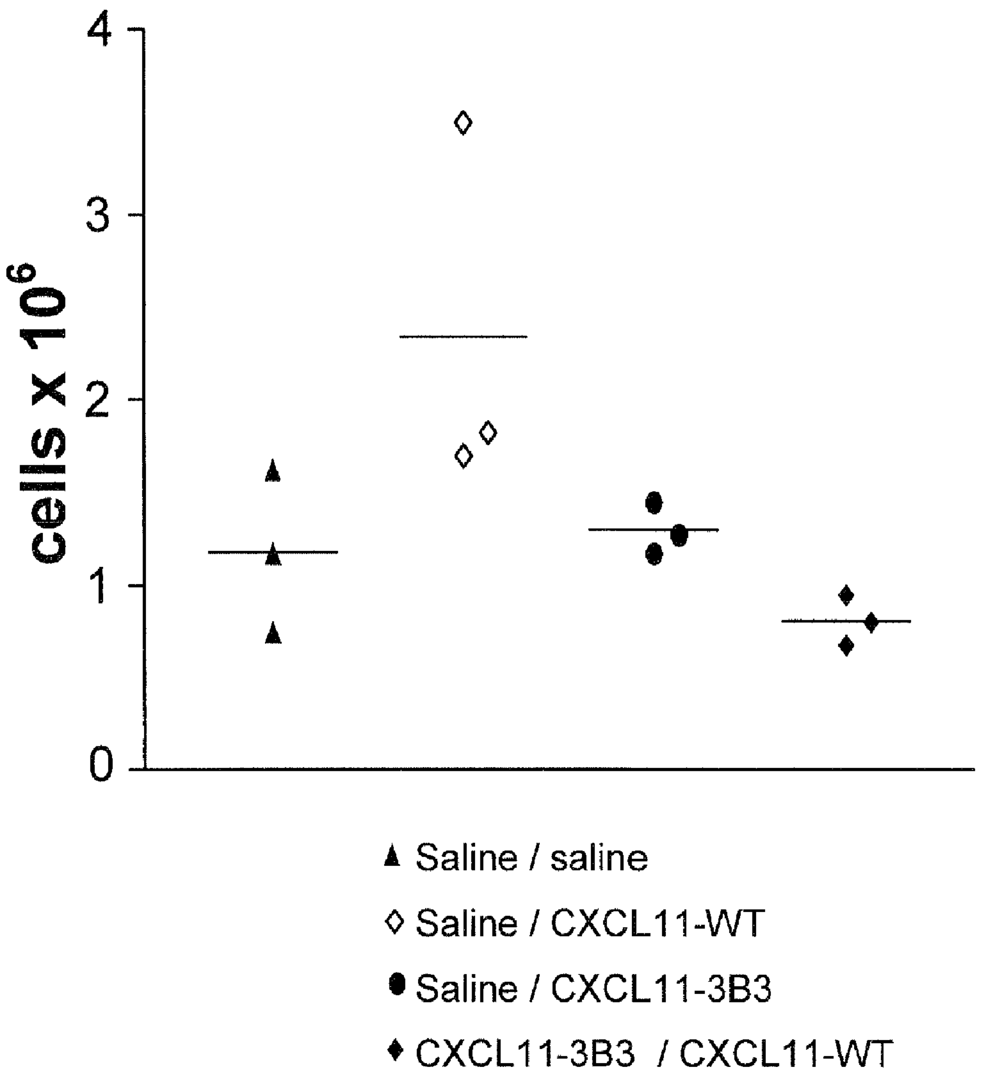
FIG. 6: graph summarizing the results on the ability of CXCL11-3B3 to inhibit cellular recruitment induced by CXCL11-WT (both administered in the amount of 10 μg). Saline or CXCL11-3B3 was administered 30 minutes prior to administration of CXCL11-WT.

It was then tested the ability of this latter mutant to inhibit CXCL11-WT in vivo (FIG. 6). CXCL11-3B3 shows no recruitment proprieties of its own, but considerable antagonistic activities over CXCL11-WT, with respect of cellular recruitment induction into the peritoneum, when prior administered at the same dose (10 μg/mouse). Therefore, the abrogation of heparin-binding in CXCL11 produces an antagonist capable of inhibiting in vivo the cellular recruitment induced by CXCL11.

Figure 7:
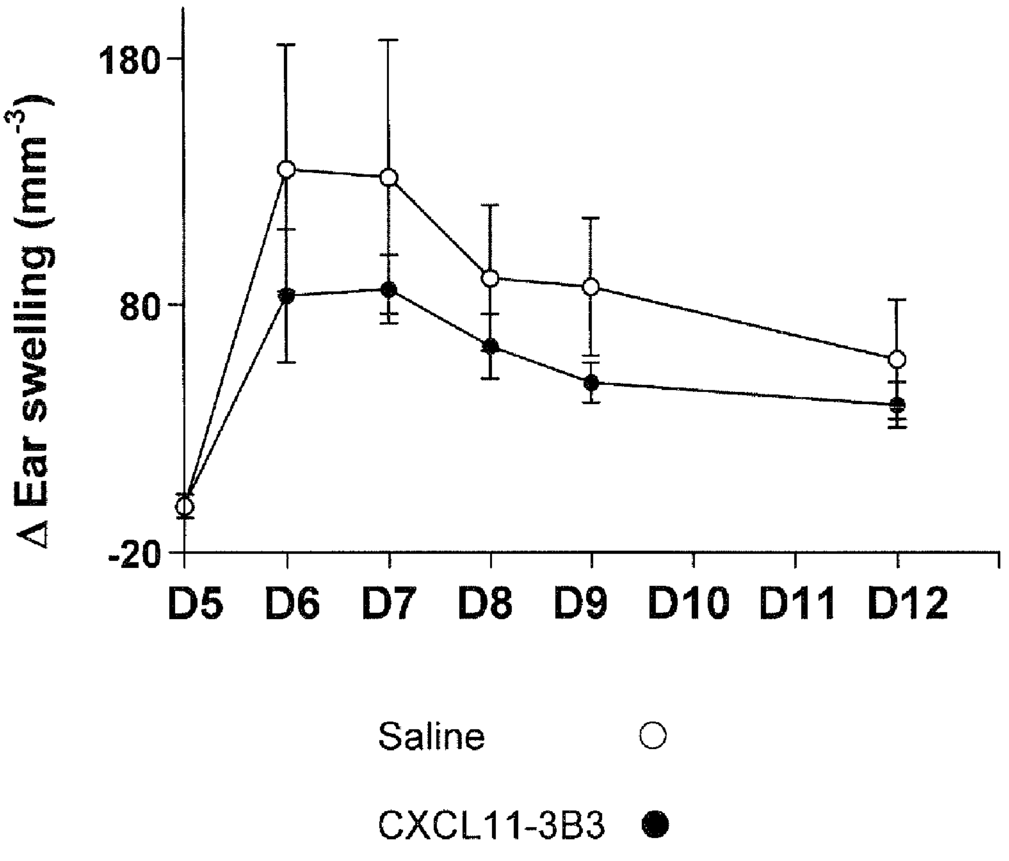
FIG. 7: graph summarizing the results on the delayed contact hypersensitivity assay using Saline, as a control, or CXCL11-3B3 at a dose of 0.5 mg/kg. The effect is measured in terms of ear swelling volume in the days following the treatment (D5, D6, D7, etc.) with a dial thickness gauge.

Finally, the properties of CXCL11-3B3 were tested in a skin inflammation model, the delayed contact hypersensitivity assay. This hapten-specific skin inflammation is mediated by T cells and generates a measurable swelling after challenging mice with the contact sensitizer 2,4-dinitrofluorobenzene (DNFB) as hapten. The induced swelling was significantly lower in mice treated with an intraperitoneal administration of CXCL11-3B3, when compared to the effect observed in mice treated with vehicle alone, throughout the treatment period (FIG. 7).

Given the results obtained in the examples of the present invention, novel antagonists of CXCR3-binding CXC chemokines can be designed on the basis of the findings of this patent application, in particular heparin-binding defective mutants of human CXCL11, human CXCL10 and human CXCL9 containing single or multiple substitutions of the conserved basic amino acids in the carboxy-terminus, and, eventually, of other basic residues conserved in one or more specific CXCR3-binding CXC chemokines and/or one or more of basic residues surrounding them.

The properties of alternative molecules disclosed in the present application can be tested by any of the methods above described, or by making use of other validating approaches known in the art, as extensively reviewed in literature ("Chemokine Protocols", Methods in Molecular Biology vol. 138, Humana Press, 2000; "Chemokine Receptors", Methods in Enzymology vol. 288, Academic Press, 1997).

TABLE I

| Amino Acid | Synonymous Group | More Preferred Synonymous Groups |
|---|---|---|
| Ala | Gly, Thr, Pro, Ala, Ser | Gly, Ala |
| Arg | Asn, Lys, Gln, Arg, His | Arg, Lys, His |
| Asn | Glu, Asn, Asp, Gln | Asn, Gln |
| Asp | Glu, Asn, Asp, Gln | Asp, Glu |
| Cys | Ser, Thr, Cys | Cys |
| Gln | Glu, Asn, Asp, Gln | Asn, Gln |
| Glu | Glu, Asn, Asp, Gln | Asp, Glu |
| Gly | Ala, Thr, Pro, Ser, Gly | Gly, Ala |
| His | Asn, Lys, Gln, Arg, His | Arg, Lys, His |
| Ile | Phe, Ile, Val, Leu, Met | Ile, Val, Leu, Met |
| Leu | Phe, Ile, Val, Leu, Met | Ile, Val, Leu, Met |
| Lys | Asn, Lys, Gln, Arg, His | Arg, Lys, His |
| Met | Phe, Ile, Val, Leu, Met | Ile, Val, Leu, Met |
| Phe | Trp, Phe, Tyr | Tyr, Phe |
| Pro | Gly, Ala, Ser, Thr, Pro | Pro |
| Ser | Gly, Ala, Ser, Thr, Pro | Thr, Ser |
| Thr | Gly, Ala, Ser, Thr, Pro | Thr, Ser |
| Trp | Trp, Phe, Tyr | Trp |
| Tyr | Trp, Phe, Tyr | Phe, Tyr |
| Val | Met, Phe, Ile, Leu, Val | Met, Ile, Val, Leu |

TABLE II

| Amino Acid | Synonymous Group |
|---|---|
| Ala | D-Ala, Gly, Aib, B-Ala, Acp, L-Cys, D-Cys |
| Arg | D-Arg, Lys, D-Lys, homo-Arg, D-homo-Arg, Met, Ile, D-.Met, D-Ile, Orn, D-Orn |
| Asn | D-Asn, Asp, D-Asp, Glu, D-Glu, Gln, D-Gln |
| Asp | D-Asp, D-Asn, Asn, Glu, D-Glu, Gln, D-Gln |
| Cys | D-Cys, S-Me-Cys, Met, D-Met, Thr, D-Thr |
| Gln | D-Gln, Asn, D-Asn, Glu, D-Glu, Asp, D-Asp |
| Glu | D-Glu, D-Asp, Asp, Asn, D-Asn, Gln, D-Gln |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Leu | D-Leu, Val, D-Val, AdaA, AdaG, Leu, D-Leu, Met, D-Met |
| Lys | D-Lys, Arg, D-Arg, homo-Arg, D-homo-Arg, Met, D-Met, Ile, D-Ile, Orn, D-Orn |
| Met | D-Met, S-Me-Cys, Ile, D-Ile, Leu, D-Leu, Val, D-Val |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Pro | D-Pro, L-I-thioazolidine-4-carboxylic acid, D-or L-1-oxazolidine-4-carboxylic acid |
| Ser | D-Ser, Thr, D-Thr, allo-Thr, Met, D-Met, Met(O), D-Met(O), L-Cys, D-Cys |
| Thr | D-Thr, Ser, D-Ser, allo-Thr, Met, D-Met, Met(O), D-Met(O), Val, D-Val |
| Tyr | D-Tyr, Phe, D-Phe, L-Dopa, His, D-His |
| Val | D-Val, Leu, D-Leu, Ile, D-Ile, Met, D-Met, AdaA, AdaG |

TABLE III

| Protein | Heparin Chromatography: Eluting concentration [NaCl] | Heparin Chromatography: Difference from CXCL11-WT [NaCl] | Mono S Chromatography: Eluting concentration [NaCl] | Mono S Chromatography: Difference from CXCL11-WT [NaCl] | Difference between Heparin and MonoS [NaCl] |
|---|---|---|---|---|---|
| CXCLII-WT | 0.77M | — | 1.08M | — | −0.31M |
| CXCLII-1B3 | 0.72M | 0.05M | 0.85M | 0.23M | −0.18M |
| CXCLII-2B3 | 0.64M | 0.13M | 0.97M | 0.11M | 0.02M |

TABLE III-continued

| | Heparin Chromatography | | Mono S Chromatography | | Difference between |
|---|---|---|---|---|---|
| Protein | Eluting concentration [NaCl] | Difference from CXCL11-WT [NaCl] | Eluting concentration [NaCl] | Difference from CXCL11-WT [NaCl] | Heparin and MonoS [NaCl] |
| CXCLII-3B3 | 0.44M | 0.33M | 0.85M | 0.23M | 0.10M |
| CXCLII-4B4 | 0.62M | 0.15M | 1.14M | −0.06M | 0.22M |

REFERENCES

Agostini C, et al. J Immunol, 161:6413-6420, 1998.
Ali S et al., Biochem J, 358: 737-745, 2001.
Baggiolini M et al., Annu Rev Immunol, 15: 675-705, 1997.
Baggiolini M, J Intern Med, 250: 91-104, 2001.
Brown A et al., J Pept Sci, 2:40-46, 1996.
Cleland J L et al., Curr Opin Biotechnol, 12: 212-9, 2001.
Cole K, et al. J Exp Med. 187:2009-2021, 1998.
Cole A, et al. J Immunol, 167:623-627, 2001.
Dougherty D A, Curr Opin Chem Biol, 4: 645-52, 2000.
Fernandez E J and Lolis E, Annu Rev Pharmacol Toxicol, 42:469-499, 2002.
Flier J et al., J Pathol, 194: 398-405, 2001.
Frigerio S et al., Nat Med, 8: 1414-20, 2002.
Garrigue J L et al., Contact Dermatitis, 30: 231-237, 1994.
Golebiowski A et al., Curr Opin Drug Discov Devel, 4: 428-34, 2001.
Haskell C A et al., Curr Opin Invest Drugs, 3 399-455, 2002.
Hoogewerf A J et al., Biochemistry, 36: 13570-13578, 1997.
Hruby V J and Balse P M, Curr Med Chem, 7: 945-970, 2000.
Kane J F, Curr Opin Biotechnol, 6: 494-500, 1995.
Kao J et al., Circulation, 107: 1958-61, 2003.
Kuschert G et al., Biochemistry, 38: 12959-12968, 1999.
Lambeir A, et al. J Biol Chem, 276: 29839-29845, 2001.
Lane B R et al., Virology, 307: 122-34, 2003.
Loetscher P and Clark-Lewis I, J Leukoc Biol, 69: 881-884, 2001.
Lortat-Jacob H et al., Proc Natl Acad Sci U S A, 99: 1229-1234, 2002.
Lu B, et al., Eur J Immunol, 29: 3804-3812, 1999.
Luo B and Prestwich G D, Exp Opin Ther Patents, 11: 1395-1410, 2001.
Luster A et al., J Exp Med, 182: 219-231, 1995.
Mach F et al., J Clin Invest, 104: 1041-1050, 1999.
Meyer M, et al. Eur J Immunol, 31: 2521-2527, 2001.
Murphy L R et al., Protein Eng, 13: 149-52, 2000.
Nilsson J et al., Protein Expr Purif, 11: 1-16, 1997.
Patel D et al., Clin Immunol, 99: 43-52, 2001.
Pillai O and Panchagnula R, Cur Opin Chem Biol, 5: 447-451, 2001
Proudfoot A, et al. Immunol Rev, 177: 246-256, 2000.
Proudfoot A, et al. J Biol Chem 276: 10620-10626, 2001.
Robledo M M et al., J Biol Chem, 276: 45098-105, 2001.
Rogov S I and Nekrasov A N, Protein Eng, 14: 459-463, 2001.
Romagnani P et al., J Am Soc Nephrol, 10: 2518-2526, 1999.
Romagnani P et al., J Clin Invest, 107: 53-63, 2001.
Romagnani P et al., Am J Pathol, 161: 195-206, 2002.
Sasaki S et al., Eur J Immunol, 32: 3197-205, 2002
Sauty A, et al. J Immunol, 162: 3549-3558, 1999.
Sauty A, et al. J Immunol, 167: 7084-7093, 2001.
Sawyer T K, in “Structure Based Drug Design”, edited by Veerapandian P, Marcel Dekker Inc., pg. 557-663, 1997.
Schwarz M K and Wells T N, Curr Opin Chem Biol, 3: 407-417, 1999.
Sorensen T et al., J Clin Invest, 103: 807-815, 1999.
Trentin L et al., J Clin Invest, 104: 115-121, 1999.
Villain M et al., Chem Biol, 8: 673-679, 2001.

The invention claimed is:

1. An isolated polypeptide antagonist of CXCR3-binding CXC chemokines, said antagonist comprising a mutant of CXCL11 in which:

a) at least one of the following basic residues, numbered on the sequence of human mature CXCL11, is substituted to Alanine, Glycine, Serine, Threonine, Proline, Glutamic Acid, Glutamine, Aspartic Acid, or Asparagine: 46, 62, or 70;

b) at least one of the following basic residues, numbered on the sequence of human mature CXCL11, is substituted to Alanine, Glycine, Serine, Threonine, Proline, Glutamic Acid, Aspartic Acid, or Asparagine: 46, 62, 66 or 70;

c) at least one of the following basic residues, numbered on the sequence of human mature CXCL11, is substituted to Alanine, Glycine, Serine, Threonine, Proline, Glutamic Acid, Glutamine, Aspartic Acid, or Asparagine: 46, 62, 66, or 70 and at least one of the following basic residues, numbered on the sequence of human mature CXCL11, is additionally substituted to Alanine, Glycine, Serine, Threonine, Proline, Glutamic Acid, Glutamine, Aspartic Acid, or Asparagine: 49, 52, 57, 59, or 71;

d) at least one of the following basic residues, numbered on the sequence of human mature CXCL11, is substituted to Alanine, Glycine, Serine, Threonine, Proline, Glutamic Acid, Glutamine, Aspartic Acid, or Asparagine: 46, 62, 66, or 70 and at least one of the following basic residues, numbered on the sequence of human mature CXCL11, is additionally substituted to Glycine, Serine, Threonine, Proline, Glutamic Acid, Glutamine, Aspartic Acid, or Asparagine: 49, 52, 57, 59, 67 or 71;

e) one of the following combinations of basic residues, numbered on the sequence of human mature CXCL11, is substituted to Alanine, Glycine, Serine, Threonine, Proline, Glutamic Acid, Glutamine, Aspartic Acid, or Asparagine:

i) 46, together with residue 49; residue 52; or residues 49 and 52;

ii) 62, together with residue 57; residue 59; or residues 57 and 59;

iii) 66 and 70, together with residue 67; residue 71; or residues 67 and 71; or iv) 62 and 66, together with one or more of the following residues: 57, 59, 67, 70, or 71;

f) at least one of the following basic residues, numbered on the sequence of human mature CXCL11, of an antagonist set forth in a), b), c) or d) is additionally substituted to Alanine, Glycine, Serine, Threonine, Proline, Glutamic Acid, Glutamine, Aspartic Acid, or Asparagine: 5, 6, 8, 17, 20, 26 or 38;

g) the basic residues of an antagonist as set forth in a), b), c), d), e) or f) are substituted with Alanine or Glycine;

h) said antagonist comprises CXCL11-2B3 (SEQ ID NO: 3), CXCL11-3B3 (SEQ ID NO: 4), or CXCL11-4B4 (SEQ ID NO: 5); or i) one or more of the first nine amino acids in the amino-terminal domain of the human mature CXCR3-binding CXC chemokine have been added, deleted, or substituted in an antagonist as set forth in a), b), c), d), e), f), g) or h).

2. The isolated polypeptide antagonist according to claim 1, wherein at least one of the following basic residues, numbered on the sequence of human mature CXCL11, is substituted to Alanine, Glycine, Serine, Threonine, Proline, Glutamic Acid, Glutamine, Aspartic Acid, or Asparagine: 46, 62, or 70.

3. The isolated polypeptide antagonist according to claim 1, wherein at least one of the following basic residues, numbered on the sequence of human mature CXCL11, is substituted to Alanine, Glycine, Serine, Threonine, Proline, Glutamic Acid, Aspartic Acid, or Asparagine: 46, 62, 66 or 70.

4. The isolated polypeptide antagonist according to claim 1, wherein at least one of the following basic residues, numbered on the sequence of human mature CXCL11, is substituted to Alanine, Glycine, Serine, Threonine, Proline, Glutamic Acid, Glutamine, Aspartic Acid, or Asparagine: 46, 62, 66, or 70 and at least one of the following basic residues, numbered on the sequence of human mature CXCL11, is additionally substituted to Alanine, Glycine, Serine, Threonine, Proline, Glutamic Acid, Glutamine, Aspartic Acid, or Asparagine: 49, 52, 57, 59, or 71.

5. The isolated polypeptide antagonist according to claim 1, wherein at least one of the following basic residues, numbered on the sequence of human mature CXCL11, is substituted to Alanine, Glycine, Serine, Threonine, Proline, Glutamic Acid, Glutamine, Aspartic Acid, or Asparagine: 46, 62, 66, or 70 and at least one of the following basic residues, numbered on the sequence of human mature CXCL11, is additionally substituted to Glycine, Serine, Threonine, Proline, Glutamic Acid, Glutamine, Aspartic Acid, or Asparagine: 49, 52, 57, 59, 67 or 71.

6. The isolated polypeptide antagonist according to claim 1, wherein one of the following combinations of basic residues, numbered on the sequence of human mature CXCL11, is substituted to Alanine, Glycine, Serine, Threonine, Proline, Glutamic Acid, Glutamine, Aspartic Acid, or Asparagine: 46, together with residue 49; residue 52; or residues 49 and 52.

7. The isolated polypeptide antagonist according to claim 1, wherein one of the following combinations of basic residues, numbered on the sequence of human mature CXCL11, is substituted to Alanine, Glycine, Serine, Threonine, Proline, Glutamic Acid, Glutamine, Aspartic Acid, or Asparagine: 62, together with residue 57; residue 59; or residues 57 and 59.

8. The isolated polypeptide antagonist according to claim 1, wherein one of the following combinations of basic residues, numbered on the sequence of human mature CXCL11, is substituted to Alanine, Glycine, Serine, Threonine, Proline, Glutamic Acid, Glutamine, Aspartic Acid, or Asparagine: 66 and 70, together with residue 67; residue 71; or residues 67 and 71.

9. The isolated polypeptide antagonist according to claim 1, wherein one of the following combinations of basic residues, numbered on the sequence of human mature CXCL11, is substituted to Alanine, Glycine, Serine, Threonine, Proline, Glutamic Acid, Glutamine, Aspartic Acid, or Asparagine: 62 and 66, together with one or more of the following residues: 57, 59, 67, 70, or 71.

10. The isolated polypeptide antagonist according to claim 1, wherein one of the following combinations of basic residues, numbered on the sequence of human mature CXCL11, is substituted to Alanine, Glycine, Serine, Threonine, Proline, Glutamic Acid, Glutamine, Aspartic Acid, or Asparagine: 66 and 70, together with residue 67; residue 71; or residues 67 and 71.

11. The isolated polypeptide antagonist according to claim 1, wherein at least one of the following basic residues, numbered on the sequence of human mature CXCL11, of an antagonist set forth in a), b), c) or d) is additionally substituted to Alanine, Glycine, Serine, Threonine, Proline, Glutamic Acid, Glutamine, Aspartic Acid, or Asparagine: 5, 6, 8, 17, 20, 26 or 38.

12. The isolated polypeptide antagonist according to claim 1, wherein the basic residues of an antagonist as set forth in a), b), c), d), e) or f) are substituted with Alanine or Glycine.

13. The isolated polypeptide antagonist according to claim 1, wherein said antagonist comprises CXCL11-2B3 (SEQ ID NO: 3) CXCL11-3B3 (SEQ ID NO: 4), or CXCL11-4B4 (SEQ ID NO: 5).

14. The isolated polypeptide antagonist according to claim 1, wherein one or more of the first nine amino acids in the amino-terminal domain of the human mature CXCR3-binding CXC chemokine have been added, deleted, or substituted in an antagonist as set forth in a), b), c), d), e), f), g) or h).

15. The isolated polypeptide antagonist according to claim 1, further comprising: a) an amino acid sequence belonging to a protein sequence other than the corresponding CXCR3-binding CXC chemokine; or b) a molecule to which said antagonist is complexed or conjugated.

16. The isolated polypeptide antagonist according to claim 15, wherein said amino acid sequence is selected from one or more of these protein sequences: extracellular domains of membrane-bound protein, immunoglobulin constant region, multimerization domains, extracellular proteins, signal peptide-containing proteins, or export signal-containing proteins.

17. The isolated polypeptide antagonist according to claim 15, wherein said antagonist is complexed or conjugated to a molecule chosen from radioactive labels, biotin, fluorescent labels, cytotoxic agents, or drug delivery agents.

18. A composition comprising a pharmaceutically acceptable carrier and a polypeptide antagonist according to claim 1.

19. An isolated polynucleotide encoding a polypeptide according to claim 1.

20. A vector comprising a polynucleotide encoding a polypeptide according to claim 1.

21. An isolated host cell comprising a polynucleotide encoding an a polypeptide according to claim 1.

22. A method of making a polypeptide comprising culturing a host cell comprising a polynucleotide encoding a polypeptide according to claim 1 under conditions that allow for the expression of said polypeptide.

23. The method according to claim 22, further comprising isolating said polypeptide.

* * * * *

UNITED STATES PATENT AND TRADEMARK OFFICE

CERTIFICATE OF CORRECTION

PATENT NO. : 7,541,435 B2
APPLICATION NO. : 10/517726
DATED : June 2, 2009
INVENTOR(S) : Amanda Proudfoot and Marie Kosco-Vilbois It is certified that error appears in the above-identified patent and that said Letters Patent is hereby corrected as shown below:

Column 2,
Line 30, "tubercolosis" should read --tuberculosis--.

Column 3,
Line 52, "established that is not possible" should read --established that it is not possible--.

Column 4,
Lines 13-14, "mutants having not only have a considerably" should read --mutants having not only a considerably--.

Column 5,
Line 4, "pico microMolar" should read --pico -/microMolar--.

Column 6,
Line 25, "to Alanine" should read --with Alanine--.
Line 30, "substituted to" should read --substituted with--.
Line 43, "substituted to" should read --substituted with--.
Line 49, "substituted to" should read --substituted with--.
Line 67, "substituted to" should read --substituted with--.

Column 7,
Lines 41-42, "of some of basic" should read --of some of the basic--.
Lines 44-45, "of these group of chemokines" should read --of these chemokines--.

Column 8,
Line 66, "or im proving" should read --or improving--.

Column 9,
Line 17, "proteinsu" should read --proteins"--.

Column 10,
Line 34, "compounds of present invention" should read --compounds of the present invention--.

UNITED STATES PATENT AND TRADEMARK OFFICE

CERTIFICATE OF CORRECTION

PATENT NO. : 7,541,435 B2

APPLICATION NO. : 10/517726
DATED : June 2, 2009
INVENTOR(S) : Amanda Proudfoot and Marie Kosco-Vilbois It is certified that error appears in the above-identified patent and that said Letters Patent is hereby corrected as shown below:

Column 12,
Line 8, "Many books and reviews provides" should read --Many books and reviews provide--.
Line 40, "derived form viral" should read --derived from viral--.

Column 15,
Line 2, "to which is administered" should read --to which it is administered--.
Lines 60-61, "the desiredr results" should read --the desired results--.

Column 22,

| | | |
|---|---|---|
| Table III, "CXCLII-WT | should read | --CXCL11-WT |
| CXCLII-1B3 | | CXCL11-1B3 |
| CXCLII-2B3" | | CXCL11-2B3--. |

Column 23,

| | | |
|---|---|---|
| Table III, "CXCLII-3B3 | should read | --CXCL11-3B3 |
| CXCLII-4B4" | | CXCL11-4B4--. |

Signed and Sealed this

First Day of September, 2009

David J. Kappos

David J. Kappos
*Director of the United States Patent and Trademark Office*

SEQUENCE LISTING

```
<160> NUMBER OF SEQ ID NOS: 8

<210> SEQ ID NO 1
<211> LENGTH: 73
<212> TYPE: PRT
<213> ORGANISM: Homo sapiens

<400> SEQUENCE: 1

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45
```

-continued

```
Lys Gly Gln Arg Cys Leu Asn Pro Lys Ser Lys Gln Ala Arg Leu Ile
    50                  55                  60

Ile Lys Lys Val Glu Arg Lys Asn Phe
65                  70


<210> SEQ ID NO 2
<211> LENGTH: 73
<212> TYPE: PRT
<213> ORGANISM: Artificial sequence
<220> FEATURE:
<223> OTHER INFORMATION: Antagonists of human CXCL11 having alanine
      substitutions

<400> SEQUENCE: 2

Phe Pro Met Phe Ala Ala Gly Ala Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70


<210> SEQ ID NO 3
<211> LENGTH: 73
<212> TYPE: PRT
<213> ORGANISM: Artificial sequence
<220> FEATURE:
<223> OTHER INFORMATION: Antagonists of human CXCL11 having alanine
      substitutions

<400> SEQUENCE: 3

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Ala Glu Asn
        35                  40                  45

Ala Gly Gln Ala Cys Leu Asn Pro Lys Ser Lys Gln Ala Arg Leu Ile
    50                  55                  60

Ile Lys Lys Val Glu Arg Lys Asn Phe
65                  70


<210> SEQ ID NO 4
<211> LENGTH: 73
<212> TYPE: PRT
<213> ORGANISM: Artificial sequence
<220> FEATURE:
<223> OTHER INFORMATION: Antagonists of human CXCL11 having alanine
      substitutions

<400> SEQUENCE: 4

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45
```

-continued

```
Lys Gly Gln Arg Cys Leu Asn Pro Ala Ser Ala Gln Ala Ala Leu Ile
    50                  55                  60

Ile Lys Lys Val Glu Arg Lys Asn Phe
65                  70


<210> SEQ ID NO 5
<211> LENGTH: 73
<212> TYPE: PRT
<213> ORGANISM: Artificial sequence
<220> FEATURE:
<223> OTHER INFORMATION: Antagonists of human CXCL11 having alanine
      substitutions

<400> SEQUENCE: 5

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Ala Ala Val Glu Ala Ala Asn Phe
65                  70


<210> SEQ ID NO 6
<211> LENGTH: 77
<212> TYPE: PRT
<213> ORGANISM: Homo sapiens

<400> SEQUENCE: 6

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Met Ser Lys Arg Ser Pro
65                  70                  75


<210> SEQ ID NO 7
<211> LENGTH: 103
<212> TYPE: PRT
<213> ORGANISM: Homo sapiens

<400> SEQUENCE: 7

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Trp Glu Lys Gln Val Ser Gln Lys Lys Lys Gln Lys Asn Gly
65                  70                  75                  80
```

-continued

```
Lys Lys His Gln Lys Lys Lys Val Leu Lys Val Arg Lys Ser Gln Arg
                85                  90                  95

Ser Arg Gln Lys Lys Thr Thr
            100


<210> SEQ ID NO 8
<211> LENGTH: 79
<212> TYPE: PRT
<213> ORGANISM: Mus Musculus

<400> SEQUENCE: 8

Phe Leu Met Phe Lys Gln Gly Arg Cys Leu Cys Ile Gly Pro Gly Met
1               5                   10                  15

Lys Ala Val Lys Met Ala Glu Ile Glu Lys Ala Ser Val Ile Tyr Pro
            20                  25                  30

Ser Asn Gly Cys Asp Lys Val Glu Val Ile Val Thr Met Lys Ala His
        35                  40                  45

Lys Arg Gln Arg Cys Leu Asp Pro Arg Ser Lys Gln Ala Arg Leu Ile
    50                  55                  60

Met Gln Ala Ile Glu Lys Lys Asn Phe Leu Arg Arg Gln Asn Met
65                  70                  75
```